US008721673B2

(12) United States Patent (10) Patent No.: US 8,721,673 B2
Mukhina et al. (45) Date of Patent: May 13, 2014

(54) METHOD OF ACUPUNCTURE AND A NEEDLE FOR CARRYING OUT SAID METHOD

(75) Inventors: Mariat Muradalievna Mukhina, Tver (RU); Nikolay Veniaminovich Chadaev, Tver (RU)

(73) Assignee: Frey Medical Technologies AG, Lausanne (CH)

( * ) Notice: Subject to any disclaimer, the term of this patent is extended or adjusted under 35 U.S.C. 154(b) by 308 days.

(21) Appl. No.: 12/599,354

(22) PCT Filed: May 7, 2008

(86) PCT No.: PCT/RU2008/000285
§ 371 (c)(1),
(2), (4) Date: Nov. 24, 2009

(87) PCT Pub. No.: WO2008/136709
PCT Pub. Date: Nov. 13, 2008

(65) Prior Publication Data
US 2010/0137896 A1 Jun. 3, 2010

(30) Foreign Application Priority Data
May 7, 2007 (RU) ................................ 2007117021

(51) Int. Cl.
*A61B 17/34* (2006.01)
(52) U.S. Cl.
USPC ........................................................ 606/189
(58) Field of Classification Search
USPC ......... 606/185–189, 139, 142, 151, 213, 217, 606/219–221
See application file for complete search history.

(56) References Cited

U.S. PATENT DOCUMENTS 5,465,593 A 11/1995 Takasu

FOREIGN PATENT DOCUMENTS

CA 2 616 134 A 1/2007
EP 1911431 A 4/2008
(Continued)

OTHER PUBLICATIONS

Examination Report issued by NewZealand Patent Office for corresponding New Zealand application 581574 dated Aug. 30, 2011.
(Continued)

*Primary Examiner* — Kathleen Holwerda
*Assistant Examiner* — Sarah W Aleman
(74) *Attorney, Agent, or Firm* — Frommer Lawrence & Haug LLP; Ronald R. Santucci

(57) ABSTRACT

The invention relates to medicine, in particular to reflexotherapy and can be used for producing long-term acupuncture action on a patient body. The inventive method for prolonged acupuncture treatment consists in determining acupuncture loci, in selecting the needle input and output points, in passing the needle through the selected needle input and output points, in keeping both needle ends outside the patient's skin, in securing the needle in this position by means of locks mounted on the needle ends and, after finishing the acupuncture session, leaving the needle in the patient's body for a specified time. Said method is characterised in that acusal tracts are formed in different histological layers of the patient's tissue by introducing needles and the points, situated in the area of the acupuncture loci and/or reflexogenic zone and/or indifferent zone, are selected as the input and/or output points for each needle. Said invention makes it possible to non-medicamentally treat the extended range of diseases and to increase the efficiency of prolonged acupuncture. Said method is carried out by using relatively simple and inexpensive facilities and makes it possible to carry out the efficient treatment practically devoid of side effects, thereby ensuring the extended use thereof in medical practice.

11 Claims, 1 Drawing Sheet

(56) References Cited

FOREIGN PATENT DOCUMENTS

Figure 1:
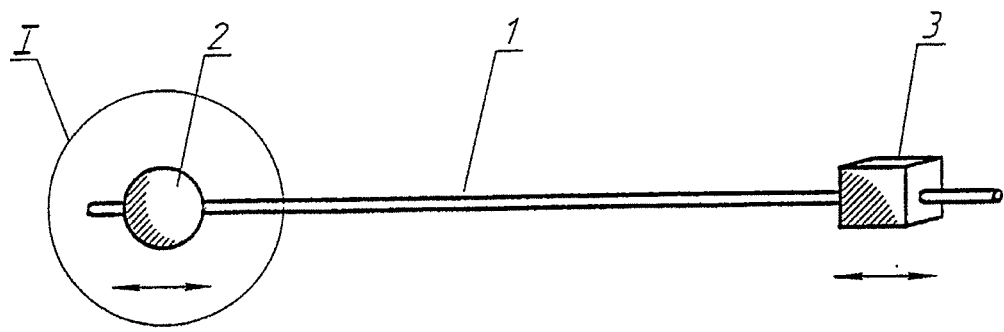

| | | |
|---|---|---|
| GB | 2 241 147 A | 8/1991 |
| JP | 8-98708 A | 4/1996 |
| RU | 26402 U | 12/2004 |
| RU | 52 330 U1 | 3/2006 |
| RU | 2 286 133 C1 | 10/2006 |
| RU | 2 289 391 C2 | 12/2006 |
| RU | 66 955 U1 | 10/2007 |
| SU | 1395324 A | 5/1988 |
| SU | 1505548 A | 9/1989 |
| SU | 1657185 A | 6/1991 |
| WO | WO 98/35646 A | 8/1998 |
| WO | WO 2007/011266 A | 1/2007 |

OTHER PUBLICATIONS

Documentary Conclusion issued by Georgian Patent Office for corresponding application, includes English translation, dated Dec. 22, 2011.

Search Report issued by Georgian Patent Office for corresponding application, includes English translation, dated Dec. 22, 2011.

Office action issued by Canadian Patent Office for corresponding Canadian application No. 2,686,797 dated May 23, 2012.

METHOD OF ACUPUNCTURE AND A NEEDLE FOR CARRYING OUT SAID METHOD

This application is a 371 of PCT/RU2008/000285filed on May 7, 2008, published on Nov. 13, 2008 under publication number WO 2008/136709 A which claims priority benefits from Russian Patent Application Number 2007117021 filed May 7, 2007, the disclosure of which is incorporated herein by reference.

TECHNICAL FIELD

An invention relates to the field of medicine, and particularly to reflexotherapy and can be used for a prolonged acupunctural action upon an organism of a patient.

BACKGROUND ART

At present a question of developing and optimization of such methods of treatments, which exclude invasion of medical preparations, chemical substances is put. Topicality of this trend is related to the growth of allergic reactions, exhaustion of immune mechanisms, development of dysbacetriosis and drug disease in a human organism in response to unjustified frequent use of pharmacological preparations, as well as deteriorating ecological situation due to the growth of technogenic impurities as a result of intensive development of industry. Acupuncture—piercing biologically active points with a help of a needle—is referred to such methods of treatment.

A scientific thought develops ancient technologies of Chinese medicine, which were known already 5000 years ago. At present the development of methods of treatment based on acupuncture goes on both in the direction of revealing new biologically active points and zones, used during acupunctural action, and selection of the most optimal modes and methods of acupunctural action for treating separate diseases, and in the direction of improving a technical base, used by reflexotherapist applying needles. One of such directions is development of the methods of treatment with the use of prolonged acupuncture action upon a patient's organism. Upon that, an action caused by needles left in patient's tissues for a certain period after the end of reflexotherapy session is understood by the prolonged acupuncture action.

Known is a method of prolonged acupuncture action, at which the prolonged acupuncture action is carried out by means of piercing an ear of a patient in an acupuncture point by a pierced earring (patent U.S. Pat. No. 5,465,593, A 44C 7/00. Published on Nov. 14, 1995). In the above method the action by a needle is made only in one acupuncture point, which does not allow to provide a sufficiently intensive prolonged action, with the intensity decreasing in time due to adaptation effect. Besides, the proposed method has a limited sphere of application.

The closest analogue to the applied method, selected as a prototype, is a method of prolonged action upon acupuncture points lying in determination of points of acupuncture, one of which is selected as a point of needle entry, and the other as the point of its exit, after which these points are pierced by way of threading them by one needle and are fixed by a locking member, installed at the end at the place of its exit on the skin surface (patent RU 2289391, A61H 39/00, published on Dec. 20, 2006). Thus the formation of a treatment channel between two acupuncture points is provided with the needle in the channel staying for a long time (a year and more).

The above method permitting to increase the intensity of prolonged action and to partially overcome the effect of adaptation, found a wide application in medical practice for treating obesity with the treatment channel being formed by way of piercing 2 points AT17 and AT 18 by one needle on the auricle in the zone of antilobium, fixing the needle in this position and leaving it in the auricle for several months and more. About 12000 patients were treated according to this technology during three years with a positive result reached in more than 80% of the patients. At the same time the results of treatment turned out to be lower than expected in about an order of 15-20% of patients due to the observed rejection of a needle. A necessity was also left in taking additional measures for securing an optimal dosing of force of acupuncture action and overcoming the effect of adaptation due to its negative influence upon the effectiveness of treatment with the use of prolonged acupuncture action. Besides, the use of this method in treating some nosological entities can create problems in respect of the selection of suitable formulization, as recommended acupuncture points can be rather far from each other, which creates an obstacle for action by "threading by one needle", and, correspondingly, limits variability in the selection of points.

ESSENCE OF INVENTION

A technical task solved by the proposed invention is the creation of a method of acupuncture with a prolonged action permitting to provide an increase of the treatment effect by way of overcoming the effect of adaptation, changing the intensity of reflexogenic action and preventing complications, as well as to expand the choice of formulizations used in treating different nosological entities.

The above tasks are secured by the fact that in the known method of acupuncture with a prolonged action, in which acupuncture points are determined, entry and exit points are selected passing a needle through the selected entry and exit points, leaving both ends of a needle outside the skin of a patient, fixing the needle in this position by means of locking members installed at the ends of the needle, and leaving the needle in the body of a patient for an assigned time after the end of the acupuncture session, the novel is that acusal tracts are formed in different histological layers of patient's tissues by way of introducing needles, and points located in the region of an acupuncture point and/or reflexogenic zone and/or indifferent zone are selected as entry and/or exit points for each needle.

Besides, a histological layer is selected from the group, including: epidermal layer, epidermis membrane, papillary layer, reticular layer, epichondral layer, cartilaginous layer, subcutaneous fat layer, muscle layer, ligaments, fascia or tendon.

Besides, in conducting an acupuncture session needles for forming acusal tracts are installed in only one of the histological layers of patient's tissues, and the acusal tracts formation in other tissues is performed by introducing needles in subsequent acupuncture sessions.

Besides, in conducting an acupuncture session needles for forming acusal tracts are installed in different histological layers of patient's tissues.

Besides, in conducting an acupuncture session installation of needles for forming acusal tracts in one or several histological layers of tissues is carried out after needle extraction, installed during a previous session.

Besides, in conducting an acupuncture session installation of needles for forming acusal tracts in one or several histological layers of tissues is carried out without needles extraction, installed during a previous session.

Besides, for needle fixation at least one moving locking member installed on the body of the needle with a possibility of sliding is used, and its fixation in the assigned position is carried out by means of plastic deformation of the needle body.

Besides, a needle is equipped with locking members, installed on needle ends, whereby at least one of the locking members is made movable and installed with a possibility of sliding along needle body.

Besides, the needle body is made rigid in the form of a rod or flexible as a string.

Besides, the needle body is made of plastic metal alloy.

Formation of acusal tracts in different histological layers of patient's tissues by means of needle installation permits to change the intensity of reflexogenic action, correlated with physiological processes occurring in histological environment of acusal tracts, which on the one hand creates overcoming adaptation effect, and on the other hand permits to prevent possible complications.

Selection as entry and/or exit points of each needle of points located in the zone of acupuncture point and/or reflexogenic zone, and/or indifferent zone permits to change the intensity of reflexogenic action and expand the selection of formulizations.

Selection of a histological layer from the group, comprising: epidermal layer, epidermis membrane, papillary layer, reticular layer, epichondral layer, cartilaginous layer, subcutaneous fat layer, muscle layer, ligaments, fascia or tendon provides for overcoming the effect of adaptation at the expense of changing the intensity of reflexogenic action and contributes to prevention of possible complications.

Installation of a needle for acusal tracts formation in only one histological layer of patient's tissues and formation of acusal tracts in other layers of tissues by introducing needles during subsequent acupuncture sessions permits to more accurately regulate the intensity of reflexogenic action and prevent possible complications.

Installation of a needle for acusal tracts formation in different histological layers of patient's tissues permits to increase the intensity of reflexogenic action and expand the selection of formulizations.

Installation of a needle for acusal tracts formation in one or several histological layers of tissues, conducted without needle extraction, installed during previous session, contributes to the increase of intensity of reflexogenic action.

The use for needle fixation of at least one movable locking member installed on the needle body with a possibility of sliding, and its fixation in the assigned position by means of plastic deformation of needle body permits to provide a safe needle fixation of the patient's body during treatment, which is one of the prerequisites providing for the effectiveness of treatment and preventing possible complications.

Rigid execution of the body of the needle in the form of a rod or flexible in the form of a string permits to expand the selection of formulizations for this method.

Execution of the needle body out of plastic metal alloy permits to provide for a safe fixation of a locking member in the assigned position by means of plastic deformation of a needle.

Figure 2:
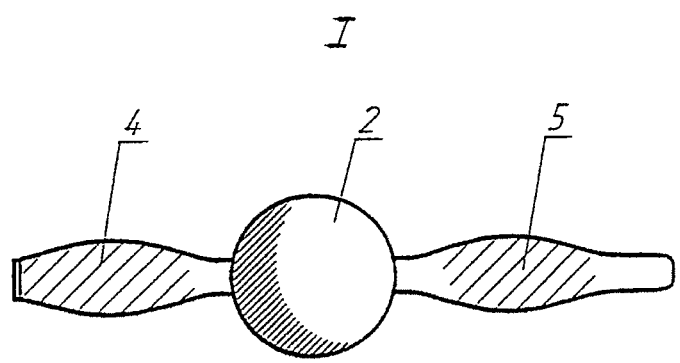

The essence of the invention is explained by the following drawings:

FIG. 1—general view of the needle;
FIG. 2—view of section I in FIG. 1 (enlarged)

PREFERRED EMBODIMENTS OF THE INVENTION

For implementation of the proposed method it is possible to use needle 1, shown in FIG. 1, which body is made rigid in the form of a rod or flexible in the form of a string. On the rod or string of needle 1 two locking members 2 and 3 are installed, placed on the opposite ends of the needle, with one of the locking members or both locking members made movable and installed with a possibility of sliding along the needle body. Fixation of movable locking members in the assigned position is made by means of plastic deformation of the end sections of the needle left outside the skin. For a safe fixation of a locking member it is enough to carry out a plastic deformation of a needle body by means of compressing it up to deformed state (flattening), for example, with a help of forceps, which is carried out from the outside (i.e. not facing the patient's body) of the locking member. After which the width of the needle at the place of compression can exceed the diameter of a reach-through hole of a movable locking member, which provides for its safe stopping. When necessary it is possible to additionally fix the locking member on the body of the needle by its flattening from the inside (i.e. contacting the patient's body) of the locking member (FIG. 2). The needle may be manufactured from different known in needle reflexotherapy plastic metals and alloys not causing an allergic reaction to metal, for example of alloy consisting of 75% of gold, 13% of silver and 12% of copper (see, for example, patent RU 26402, A61B 17/06, published on Dec.. 10, 2002). Dimensions of a needle may have different values, determined by the selection of a place of needle installation and parameters of the action.

When carrying out an acupuncture, points of acupuncture are determined in accordance with the formulizations recommended for treatment of a disease available with a patient, with entry and exit points for each needle being selected from the points located in the region of acupuncture point, and/or reflexogenic zone, and/or indifferent zone. Then needle 1 is passed through the selected entry and exit points, forming an acusal tract in a corresponding histological layer of the patient's tissues, and both ends of the needle are left outside the patient's skin. After which needle 1 is fixed in this position by means of locking members 2 and 3 installed on the needle ends, out of which at least one is movable. Movable locking members are stopped by means of compression of a corresponding outside section of the needle body (outside the locking member) up to a deformed state (flattening). Loose ends of the needle going outside the locking members' limits are cut with a help of forceps. Upon the end of acupuncture session a needle is left in a patient's body for an assigned period of time, which can exceed 1 year and more. Depending on the selected tactics of treatment several needles can be used, each of which is installed in different histological layer. However this does not exclude a variant at which one needle can be installed immediately in several histological layers. As a rule, during conducting an acupuncture session needles are installed for formation of acusal tracts in one of histological layers of a patient's tissues, and the formation of acusal tracts in other layers of tissues is performed by introducing needles in subsequent acupuncture sessions. Upon that, depending on the required dynamics of treatment, installation of needles during subsequent acupuncture sessions can be performed both extracting the needles installed during a previous session, and leaving previously installed needles, which usually contributes to reinforcement of reflexogenic action.

During selection as entry and/or exit points for each needle of points located in the zone of acupuncture point and/or reflexogenic zone and/or indifferent zone different variants can be used:
from point to point;
from point to a reflexogenic zone;

from point to indifferent zone (outside a reflexogenic zone);
from a reflexogenic zone to a point;
from a reflexogenic zone to the reflexogenic zone;
from a reflexogenic zone to indifferent zone;
from an indifferent zone to a point;
from an indifferent zone to a reflexogenic zone Upon that, variants "from point to point" and "from reflexogenic zone to reflexogenic zone" include, among others, the cases when needle entry and exit points can, correspondingly, be located within the limits of one point or one zone.

Increase of variability in the selection of entry and exit points expand the range of acusal tract formation and, correspondingly, possibilities of the method in part of selection of formulizations for treatment of different nosological entities, as well as permits to provide a more selective action and overcome an adaptation effect in the process of prolonged action.

Upon that, in the description of the applied method a notion of "reflexogenic zone" known from the state of the art is used, for example, from monograph "Central Mechanisms of Acupuncture Therapy", N. A. Nikolaev, Riga, 1998, according to which:

under the term reflex understood is a quick response of different biological structures to a certain, specific and precisely localized irritation, arising against a will control of a man (ibid., page 6), and the main factor is a peripheral origin of any reflex;

under reflexogenic zone understood is a peripheral zone of action, which forms the beginning or end of a corresponding reflex arch, creating either diagnostic zone, or a place of application of treating action. Doctors know points, characteristic for certain diseases according to semiotics, and they also know HEAD A zones very well (ibid, page 15).

Upon that, an acupuncture point can be considered as a particular case of a reflexogenic zone. Reflex peripheral zone is point-like for the points of corporal acupuncture and auriculotherapy. Thus, point Weihe, used in homeopathy is already greater in diameter than the majority of known acupuncture points (within the limits of finger-cushion). The Hannemanna a point (also used in homeopathy) has an analogous size. Head zones are considerably more extended—their dimensions can reach up to several centimeters. The same is true of dermalgic zones Jarricot usually being round or oval along all the contour (Jarricot H., 1932—*Sur certains etats douloureux: visceralgies, dermalgies reflexes, cellules et quelques phenomenes reflexes d origine theraputique Essai clinique et therautique*. These de medicine, Lyon).

In treating patients with the use of the applied method the work was basically carried out with dermalgic zones (pain zones on the skin having links with the internal organs and systems).

A layer, comprising: epidermal layer, epidermis membrane, papillary layer, reticular layer, epichondral layer, cartilaginous layer, subcutaneous fat layer, muscle layer, ligaments, fascia or tendon is selected as a histological layer.

Upon that it should be pointed out that the "channel" formed according to the claimed method is not related to acupuncture channels or meridians in the traditional understanding of meridians, adopted in reflexotherapy. In difference from usual acupuncture channels, which by a conceptual non material line connect energetic flows between strictly defined points, it mechanically connects any separately taken acupuncture points according to formulizations prepared by a doctor, and in the place of needle location as a result of epithelization processes a material channel is actually formed. In connection with that in order to underline the difference of the above channel from the traditional notion of "acupuncture channel", the term "acusal tract" (from Latin "acus"—needle) proposed by the author is used in the present description.

A mechanism of prolonged action of such treatment channel as "acusal tract" can be described in the following way. As it is known when installing needles for a long time (prolonged action) an adaptation to reflexogenic action appears, which reduces the efficiency of treatment and increasing the recovery time. Formation of "acusal tract" by the claimed method provides for maintaining a required intensity of reflexogenic action in the tract during rather a long period of time, permitting to avoid inflammatory complications thereby. Upon that, the intensity of reflexogenic action in the tract has a tendency towards cascade increase, as it is pro-gradiently correlated with physiological processes taking place in histological media in a place of the needle location. Directly, at the moment of needle introduction itself, a primary flow of pulses is formed as it is known. Then after passing a needle through the selected points (threading of points) secondary flows of pulses are formed, which are more powerful, permanent and prolonged. These flows of secondary pulses from reflexogenic zone are stipulated by physiological processes occurring in tissues. Upon that, it is possible to distinguish 3 stages of processes occurring in tissues, and correspondingly, pulses, arising at each stage are subdivided in three types:

1 Stage—Epitalization of Acusal Tract. Up to 30 Days.

As a result of acusal tract formation an acusal tract space with two holes formed by a needle is created. According to regeneration laws tissues around needle start to epitalize, forming epitalized channel. In the process of epithelium growth in the course of a gradual and long epitalization cell receptors generate a powerful flow of secondary micro-pulses of the $1^{st}$ type from a reflexogenic zone to the lower centers of hypothalamo-pituitary axis, which increases the effect of this action. In particular, in treating fattening, an inhibition focus is created more quickly in the center of hunger in hypothalamus, and lipolytic mechanisms are activated and as a result a body mass is reduced. In treating an arterial hypertension afferent pulses potentiate angio-suppressive effect in a vessel motion center in hypothalamus and arterial pressure is normalized more quickly. In case of allergy treatment an activity of anti-hystamine mechanisms is increased, which more rapidly jigulate allergic reaction. For patients with a longer anemnisis and an expressed degree of a disease, for which a more prolonged action is required, from one up to several months, an important therapeutical moment is the action by secondary pulses of the second types, which are produced at stage 2.

Stage 2—Acupuncture Channel Regeneration

When epithelization of acusal tract is finished, the surface of the channel formed will be covered by multi-layer flat cornified epithelium; epidermis—external layer of cells of which is gradually exfoliating. Renewal of epidermis occurs at the expense of malpighian layer ("Anatomy of a Man", Borzyak E. I. et al., volume 2, Moscow, Medicine, 1987, page 469). This process of epidermis cells regeneration is a powerful irritant of exteroreceptors, transforming irritation energy into nervous pulses, determining a powerful flow of neurogenic afferent pulsation ("Anatomy of a Man", Borzyak E. I. et al., volume 2, Moscow, Medicine, 1987, page 290) to the nuclei of a brain marrow. According to reflector theory, generally accepted in medicine—the more pulses are from periphery, the more expressed are the processes in central structures—ganglionic nodes, lower centers of the brain marrow. Thus, secondary pulsation of the $2^{nd}$ type contributes to the treatment effect reinforcement.

$3^{rd}$ Stage—Intra-Channel Extumeoation (Ex-Tumeo—Bulge—Latin)

In case of leaving a needle in the acusal tract from 4 months and more in the channel gal formed are accumulations of exfoliated cells of epidermis, neutrophiles and macrophages, perished bacteria. In practice when removing a needle at this stage there is a whitish deposit on it, and sometimes this deposit in the form of a rod is extracted itself by pressing a tampon to the acusal tract outer wall. With time a gradual accumulation of the above products of microorganisms vital activity will take place and at the extent of filling of acusal tract by products of vital activity of tissues structures a pressure on its internal walls is created with an effect of spreading, and the longer the needle stays in the channel, the more accumulated content of the channel will press upon its walls and, consequently, the more expressed will be a passive pressing pulsation. These impulses are classified as secondary impulses of the $3^{rd}$ type. They contribute to maintaining a dominant, formed in the preceding stage as well as potentiate the treatment effect. Upon that, as the acusal tract is a through tract and an outflow of exudate and output of utilized organells, cells and other products of life activity of microorganisms on the surface of the skin is provided, there will be no extra stagnation phenomena in the channel, and, correspondingly, formation of conditions for the development of inflammatory complications.

However, during introduction of a needle and acusal tract formation in one of the skin layers, after a certain period of time, individual for each particular patient, again the habituation of receptors of the acusal tract takes place, i.e. adaptation to the number and force of pulses occurs. In order to overcome this effect it is necessary to consequently or simultaneously reinforce the flow of pulses. For this it is proposed to form acusal tracts in different histological layers of patient's tissues, for example, consequently pass an epidermal layer of the skin, papillary layer, reticular layer, subcutaneous fat layer. A selection of histological layers of patient's tissues for formation of acusal tracts is determined based on both peculiarities of the patient's organism and a character of his disease, and taking into account the specifics of each histological layer from the point of view of its applicability to the purposes of prolonging needle reflexotherapy. Meanwhile, each histological layer has its own peculiarities of structure, innervation and blood circulation, as well as its cellular composition. The use of these peculiarities allows to obtain a new technical result.

It is recommended to start the installation of needles from epidermal layer of the skin. Then, after determining needle entry and exit points, located in the region of acupuncture point, and/or reflexogenic zone, and/or indifferent zone, a needle is introduced into epidermal skin layer, led to the surface and is fixed, and then it is left in this position for a certain period of time, depending on nosology. Then at the next session the needle is removed or left where it was, if it is necessary to strengthen the action. A criterion for location of the needle in this skin layer is visualization of a needle rod from under the epidermal cells. A result of needle introduction into this layer will be the creation of a softer and finer pulsation for a careful beginning of treatment, as well as a possibility of conducting a trial treatment, in order not to provoke aggravation of the disease due to too powerful pulsation or any other complications from needle acupuncture, i.e. for checking the reaction of an organism to acupuncture. The necessity of such approach is caused by the problem of individual intolerance of acupuncture in some patients, about which all manuals in acupuncture warn. At such reaction, after the needle introduction a patient is covered with cold sweat, becomes pale and looses conscience. In the basis of etiological mechanism of this pathological reaction lies the formation of a powerful flow of afferent pulses, which happens in the acupuncture zone under the influence of a needle. By a centripetal flow the pulses are going to hypothalamo-pituitary axis, into vegetative centers located there, which do not cope with this information and a failure occurs, which is revealed in the above symptoms. Upon that,—the basic recommendation is to remove needles as in this case it is considered unilaterally that with these symptoms acupuncture is contraindicative and a patient is deprived of a doctor's assistance by such effective way as acupuncture. Action upon an epidermal layer solves the task of preparation of an organism and vegetative centers to the flow of afferent pulsation and prevents possible pathological reactions to acupuncture. As during the introduction of a needle into this skin layer pulses will be minimal, then unpleasant sensations during that will be practically zero, i.e. in other words, this can be compared to a "splinter", received by a person in everyday life, which he even have not noticed. Thus, carrying out an initial action to the epidermal layer provides for a permissive initiation of treatment and is a preventive measure for preventing a pathological reaction of an organism to acupuncture, which permits to overcome an individual intolerance of patients to acupuncture action. Then the needle is introduced into the epidermis membrane, with outputting its end to the surface of the skin and fixation by a locking member. Afterwards, there is also exposition time, which during prolonged action can constitute up to 60 days and more. In practice, a development of adaptation is noticed after 60 days.

For preventing an adaptation, increasing an effect and renewal of pulsation at a subsequent session a patient is introduced a needle by the same method, but through a papillary layer of derma. The papillary layer is characterized by sponginess, that is why during an introduction into this layer a needle will be somewhat shine through, and a hand of a doctor will be as if falling into loose connective tissue. The result of acusal tract formation in this layer will be activation of pulsation due to new receptors activation, and as well as due to biochemical processes occurring during dispersion of micro-diapedetic hemorrhages, formed during traumatization during introduction of needle into small diameter blood vessels, which are characteristic of this layer of skin. A needle is installed to a patient both with removal of the preceding one, and leaving it in the action zone. The next administration is prescribed according to the same indications.

At the next session a procedure of piercing is repeated according to the same scheme, but the action is performed into a reticular layer of derma. A needle is left for the time required for exposition. The reticular layer, in difference from the surface papillary layer, located directly under epidermis, consists of tough loose connective tissue, comprising a big amount of collagen and ellastinic fibers and small amount of reticular fibers; it is the toughest of all layers. Data about a structure of this layer of derma are given in the known sources ("Anatomy of a Man", Borzyak E. I. et al., volume 2, Moscow, Medicine, 1987, page 470). A criterion for needle fitting into this layer will be a feeling of tough tissue media and accompanying necessity to push the needle with a certain power thrust and pressure. A result of the needle action in this layer will be renewal of pulsation due to actuated new receptors and, as a consequence, prevention of adaptation.

In some cases for improving reliability of holding a needle it is recommended to install it into-sub-reticular layer, because layers of ellastinic and collagen fibers will contribute to a peculiar corset formation, which will prevent exit of the needle through the skin. The criteria of needle fitting into this layer will be a feeling of lapse of a hand into a media with lesser resistance. A better acceptance of a needle under a reticular layer is also stipulated by the fact that this needle, located under that layer, will be actually lying in subcutaneous pacefollower, comprising accumulations of fat. It is in it that a deep dermal arterial network is passing, i.e. a good blood supply takes place. This means an optimal passage of all reparative processes, as well as good trophism for formation of the above tract (channel). A deep lymphatic network also is being formed at the border with subcutaneous fatty cellular tissue, lymphatic vessels of deep network are connected to vessels of fascia, muscles, directing to regional lymphatic nodes. Thus, a good lymph outflow and an absence of stagnation phenomena in this zone will also contribute to regeneration of cells for healing and epithelialization of acusal tract. These anatomic peculiarities stipulate the reliability and strength of the walls of the tract formed for a prolonged action upon the points, as well as a reliability of a needle presence in it. It should be also pointed out that an anatomical peculiarity of sub-reticular layer is in a more expressed plexus of nervous fibers of somatic, sensitive (cranial, cerebro-spinal) and nerves of the vegetative system in the sub-reticular layer and in upper layers of subcutaneous fatty cellular tissue. It is known that in case of a good innervation more pulses will come along centripetal fibers into lower centers of the brain marrow. The more flow of pulses is created, the more expressed is a therapeutic effect from this action.

The next histological layer is a layer of subcutaneous fatty cellular tissue. This is especially acute in case of application in corporal points formulations. The same result will be reinforced in this case due to peculiarities of structure and blood supply of fatty cells, traumatization of which will increase an ejection of biologically active substances (histamines, prostaglandines), at the expense of which irritation will be even more intensive, and a traumatic effect more powerful. A flow of pulses, formed in the acusal tract, located in subcutaneous fatty cellular tissues, potentiate a treatment effect of the whole of the session.

In certain clinical cases it is recommended to conduct the above procedure in a perichondral layer. This is a lepidic tissue of a cartilage, for example, on a concha of auricle. A peculiarity of this layer is an availability of collagen fibers, located in one plane in the form of parallel beams. An acusal tract can also be formed in it for 1 year and more. The result will also be activation of new receptors, and due to that—renewal of pulsation and prevention of adaptation to acupuncture action. Taking into account a necessity in case of some nosologies of acting upon points located on the auricle, this method can be implemented in a lepidic tissue. The basis of this histological media is formed by isogenic cellular groups of chondrocytes, surrounded by intercellular homogenous substance consisting of proteinglycanes.

Important in the formulation aspect is the creation of acusal tract in a muscle layer. A peculiarity of the muscle layer is a powerful blood supply and innervation. The muscle tissue is characterized by a random contraction of muscle fibers, which have branching merging between themselves, thanks to which a developed muscle network arises. Correspondingly, a distribution of pulses is spread along all receptor zone of a muscle, which involves new receptors, strengthening pulsation and preventing a development of adaptation. At the expense of these peculiarities renewal of pulsation will be performed at the expense of switching new receptors, and consequently, preventing adaptation to acupuncture action.

The next embodiment of this method is connection of a receptor apparatus of ligaments. Tough fiber unshaped tissue of ligaments, fascia and tendon consists of fibroblasts, elastic and reticular fibers.

There are cases in practice when after producing an action upon all the above layers, it is necessary to additionally increase the pulsation and renew a character of pulses, involving new receptors. For this purpose a creation of a bent tract was used, one branch of which passes through all histological layers up to ligaments, and the other branch is outputted through the same layers, as if making a bent in ligaments. This technique permitted to reinforce the effect of the procedure at the expense of which a quick therapeutical effect was reached.

The above sequence of layers for acusal tracts formation is a recommendatory character and does not limit the selection of possible variants of the use of claimed method, because in practice the above selection, as it was indicated above, is determined based on a concrete situation and specifics of each histological layer. The proposed method also permits installation of several needles in one session in the selected histological layer.

The results of proposed method application can be illustrated by the following examples from practice.

Example A. A patient applied with complaints for irregular cycle with pains in the field of small pelvis during these days. She suffers from ovarian dysfunction for 3 years. Medication treatment is counter-indicated because of allergy to medicinal preparations. A classical acupuncture gave instable result.

A decision was taken to conduct a course of prolonged auriculotherapy with the acusal tract formation in different histological layers. Before the session of acupuncture with a help of electropuncture diagnostics the most representative points on the auricle were selected: AT55 (seng-meng), AT 58 (uterus), AT 82 (diaphragm), AT 83 (middles of the ear). Upon determining the topography of points a needle was introduced into point AT55 into a surface epithelial layer, and outputted from point AT 58, after which the needle was fixed in this position with a help of a locking member. The same was carried out with another pair of acupuncture points. Through AT 82 a needle was introduced into epithelial layer, passed in this layer and outputted from AT 83. This action permits to generate a fine flow of pulses for an introductory action upon lower level hypothalamic structures. The needles were left for 1.5 months. At the next session the needles were removed, and the action was carried out through the same points, but already in the papillary layer of derma and the needles were left for 2 more months. There are many small caliber vessels in the papillary layer, capillary loops. Under the needle action occur diapedetic hemorrhages, during dispersion of which hyperproduction of pulses due to this factor also occurs. A criterion of needle fitting into this layer can serve a feeling of damping by needle into a soft substance. The patient pointed out an improvement of a general state in the days of the cycle, reduction of pain. After removal of needles from papillary layer the needles were introduced by the above method of prolonged action into capillary layer of derma, which is a tougher layer of skin, in which elastic and collagen fibers are located, a big amount of receptors. Renewal of action to a new tissue layer increases pulsation and interferes with the development of adaptation. If it is necessary to improve the needle hold, the it is better to pierce under this layer, because this corset of collagen and ellastine fibers will hold the needle and interfere with its rejection. The needles were left for 3 months. At the session the patient informed about a stable improvement of status, but the duration of periods was still left increased for an order of 3 days. And then, a creation of an acusal bent tract was applied, going through all the layers.

The needles were left in the same formulation points for 3 more months. During this period of treatment by a new method of prolonged action the patient noticed an improvement not only of the general state, but also elimination of all pathological symptoms—periods became painless and regular. After that there were no indications for further action and the needles were removed from the auricle of the patient.

EXAMPLE 1

From a Point to a Reflexogenic Zone

A forty eight year old patient applied with aggravation of neuralgia of tregimenal nerve. Complaints for irradiating acute pains of a lumbago type to a zone of auricle and internal ear. The anamnesis included: is suffering from neuralgia of tregimenal nerve during 10 years. Attacks are provoked by over-cooling, nervous stresses. Aggravations arise, as a rule, every 1-2 months. Before that she pointed out staying in cool premises. Attacks of pain appear during the day time, but they are especially expressed at night, they are practically not stopped by pain release preparations; she is forced not to sleep and she is not able to work in the morning. Objectively: during palpation the zone of auricle an acute pain is noticed at point IG 19 (tin-goon) with irradiation to the internal ear, as well as along a zygomatic arch in the region of an orbit.

With an aim of stopping this symptoms it is necessary to conduct a long sedation of this point by the method of prolonged action. For this purpose a piercing of this point was made with subsequent outputting a needle end to the outside of the skin out of this acupuncture point, but to nearly located innervation zone of the maxillary nerve (second branch of the tregimental nerve). The needle is introduced into papillary layer of derma and fixed outside the skin by removable locking member, installed at both ends of the needle. Next session is appointed in 3 weeks. At the reception the patient did not raise complaints for a pain syndrome. According to her words there were no pain attacks at nights, she slept well, intensity of attacks and frequency decreased immediately on the next day after session, and during 3 days the attacks fully stopped. For fixing the result, taking into account a chronic character and duration of the periods of aggravation of neuralgia, the needle was left for 1.5 months more. In 1.5 months the pains did not resume and for continuation of needle placement there were no indications. The needle was removed from the acusal tract.

EXAMPLE 2

From Point to Indifferent Zone

A needle is introduced into one point with an exit to any convenient region of the skin.

A seven year old patient. He was brought to a session by his father with the complaints to random urination at night. He suffers this disease from birth. He was treated by neuropathologist by pharmaceutical preparations with no result. A classical acupuncture was conducted several times by courses without a positive dynamics. A frequency of night incontience constitutes 2-3 times per night. Objectively—pathological visible defect of urination system were not revealed, analyses are in norm. A diagnosis of sphincteric—detrusor dyssynergia was put.

With the aim of cutting short enuresis a boy was conducted a prolonged action selectively to point RP 6 (sanin-dsiao) from two sides at the internal surface of lower third of the lower leg. With this aim the needle was introduced into point RP 6, and the lower end of the needle was introduced 2 cm above to the convenient place and a locking member was put at two sides. A bandage was removed in a week. An acusal tract, formed in subcutaneous fatty cellular tissues, epithelized, skin integuments were pure, the needle moves freely in the channel, and the locking members interfere with the needle falling from the channel at two sides. Random urination after 10 days of prolonged therapy became arise not every day, and after 3 weeks 3-4 days clean gaps were observed. During subsequent 2 months a frequency of enuresis was observed once a week and the attacks smoothly boiled down to zero during 3 subsequent months, and did not resume. In 6 months the needles were removed from the acusal tracts.

EXAMPLE 3

From Indifferent Zone to a Point

An eighteen year patient applied with complains for sweating of palms. This symptom appeared in puberty period in 14 years and is increasing with age. Manifestations are strengthened in case of anxiety, which causes aggravation of the state of psycho—emotional tension and a patient experiences a deep discomfort at that. Besides, the patient is studying driving and the wheel, sliding in humid palms, subjects his life and lives of passengers to danger on the road. Among method of treatment used was a medicamental treatment for 6 months by the neurologist, and periodic courses of acupuncture reflexotherapy according to classical schemes for 1 year. Significant therapeutical results were not achieved. Objectively: the state is satisfactory. Skin integuments have normal colouring. During examination an expresses hyperhydrosis of palms and axillary zones is revealed. Pathology of internal organs was not revealed during the examination.

The most known general action point, recommended for action, in particular, during vegetative vascular dystonia—he gu (G1 4) was selected. With the aim of creating a maximum powerful flow of pulses needles were introduced from the zone adjacent to this acupuncture points and passed in different histological layers—epidermal, papillary, retinal, subcutaneous fatty cellular cells and in a muscle layer, and then outputted in the point itself to the surface of the skin and fixed by locking members. Thus, 5 acusal tracts were formed simultaneously, form which a powerful flow of pulses along afferent neurons was directed to hypothalamo-pituitary axis. There an afferent synthesis took place, pulses along efferent neurons returned to perspiratory glands, located in the retinal layer of the skin of palm surface of the wrist and axillary (underarm) region. This signal balanced dysfunction of sweat glands, namely hyper-production of secreta by glandular cells of sweat glands. As a result, more quickly then in the case of usual acupuncture a therapeutic effect was reached, namely in 2 months the reduction of sweating occurred, which caused a huge psychological discomfort to the patient. From the patient's words normalization of sweat gland secretion happened already in a weak are installation of needles by the method of prolonged action from an indifferent zone to a point.

EXAMPLE 4

From Reflexogenic Zone to Reflexogenic Zone

A thirty-four year patient applied with the complaints for long intensive headaches. She suffers from migraine from 20 years. Attacks appear spontaneously, not related to external irritants. Lately she cur short pains by strong non-narcotic analgesics, which no more help in therapeutical dosages. Objectively: the state is satisfactory; a position of the head is forced. As active movement in head turning reinforce the pain, the patient keeps her head fixed in the position with a slight inclination ahead, as in this position pain is at least stable. When examining a neck portion of the vertebral column—movements are painless in full volume. Some sponginess of a face is noticed. During the examination and palpation 2 zones behind the auricle, both with the diameter of the cushion of the little finger at the distance of 1 cm from each other are sharply painful. During topographic determination of painful zones in this region there is no single acupuncture point. Nearby there is VB 20 and VB12, however the pain epicenter in the form of 2 zones is located between these points. It was noticed that during long palpation of painful zones some analgesia takes place.

At the reception the acupuncture by the method of prolonged action was conducted into painful zones found by way of the introduction of a needle into one zone and outputting its end from other zone with subsequent needle fixation in a muscular layer with a help of locking member. The needle was left for one month. IN a months time at the reception the patient informed that the pain started to decrease during subsequent 2 hours after the session. During the whole period of needle staying the pain did not resume. The needle was left for 1 more month. At a repeated reception there were no painful attacks. The state was satisfactory. Feeling fine. The needle was removed from the channel.

EXAMPLE 5

From Reflexogenic Zone to a Point

A sixty-five year patient applied with the pain in the region of the right shoulder blade, which is reinforced during shoulder joint movement and during long fixation of monotonous position of the body. The pain is constant with irradiation to a certain region under the shoulder blade. During examination a forced position of the body attracts attention—right shoulder is a little bit lifted. Palpitorily—soft tissues on the affected side are painful, thickened. During deep palpation an area of increased density of the size of a bean seed is revealed, sharply painful. Upon that, the pain irradiates to the shoulder, neck to such an extent, that the patient even cries out. This symptoms are stipulated by the development of a trigger zone in case of a long spasm of muscular fibers on the background of osteochondrosis of the neck and breast section—trigger zones—(Shealy, C. Mortimer, J. Et Hagfor, N., 1970—Dorsal column electroanalgesia. *J. Neurosurg.*, 32, 560-564). Classical acupuncture conducted into the trigger and according to the recipe recommended in these cases gave no effect. Manual therapy is counter-indicated to the patient due to age criteria.

At the session piercing by the method of prolonged action to the zone in the trigger projection with outputting the needle in the point of local action V 45, located at a distance of 3 cm. The needle is fixed by locking members with the formation of a bent acusal tract, passing through epidermal layer, epidermis membrane, papillary, retinal, epichondral, subcutaneous fatty and muscular layer and was left for 2 weeks. After 2 weeks at the reception the patient informed that his state had improved in 3 days. From the words: "got up without pain". During examination forced position of the body is absent. A residual pain in the trigger zone is revealed by palpation. The needle was left for 2 more weeks. At the next reception the pain is practically absent, but the needle was left for 10 more weeks for effect fixation. In 2.5 months at the reception the tissues in the acupuncture zone are soft, painless. The patient feels fine. The pains did not resume.

EXAMPLE 6

From Reflexogenic Zone to Indifferent Zone

A 23 year old patient applied with the complaints to stable pain in the left side. The pain has a dull character and gradually harasses, as it does not disappear during a month. During examination of internal organs no pathology was revealed. Objectively: the state if satisfactory. A stomach is soft, painless. Physiological functions are within the norm. During palpation of the zone of the $6^{th}$ rib and intercostal space a zone of pain is revealed along the medium axillary line. Skin cover above this zone is not changed. Thickenings are absent.

A center of this elective pain was found with a help of a blunt probe, and a needle was introduced into it by the method of prolonged action outputting other end outside the pain zone limits. The end was fixed by removable locking member. The needle was left for 3 days in subcutaneous fatty layer. During examination the patient informed about fading of pain. The needle was left for 3 more days. At the reception the patient informed about substantial improvement of the state; the pain periodically appears, but as a whole "light periods became considerably greater. The patient was appointed to come to the reception in 1 month. There are no complaints at the reception. Pain completely disappeared. The needle was removed from the channel.

EXAMPLE 7

The Point Itself within its Limit

A 56 year old patient suffers from bronchial asthma during 20 years. She has regular medicament treatment in the period of aggravation: spring—autumn. Between aggravation periods she takes bronchial spasmolytic preparations. During the last 2 years the attacks are practically daily, basically in the evening time during the whole of the year. Sanatorium resort treatment, medicament treatment, classical acupuncture did not bring an expressed effect giving only temporary relief of the attacks of the bronchial spasm. Objectively: the patient has normal meals and is normally built. Skin integument has normal colouring, clean. During lung auscultation—breathing is rough, exhalation is prolonged. A frequency of breathing movements is 26 per minute, expiratory embarrassment. A question of hormonal treatment was raised.

As it is common knowledge that hormonotherapy is a therapy of "despair", it was decided to conduct a course by the method of prolonged acupuncture for the whole complex of points indicated for treatment of this nosology. For this purpose points on auricle AT 13 (adrenal gland), AT 15 (throat and larynx), AT 28 (hypophysis), AT 51 (sympatic), AT 31 (asthma), AT 55 (seng-meng) were taken. On the posterior surface of the back the following corporal points were taken V 11, V 41, V 42, V 13, V 43, V 15, V 17. A topographical zone of this point was determined for each point. IN a contour edge of the point a needle was introduced and passed through the whole of the point, then the needle was outputted from the other edge of the point, ends were fixed with removable locking members, For auricular points thin needles with the length of 205 mm were taken, which were introduced into a cartilage layer, and for corporal points—thicker ones with the length from 1 cm to 1.5 cm. The above needles were used for forming a bent acusal tract, passing through epidermal layer, epidermis membrane, papillary, retinal, epichondral, subcutaneous fatty layers and muscular layer. The needles were left in a patient for 28 days. At the next reception the patient informed about a considerable improvement of her state; frequency of attacks of bronchial spasm was reduced up to 2-3 times a week. The needles were left for 2 months more. The patient did not come for the next reception, but informed by telephone that her state is gradually improving and attacks of asphyxia trouble her 1-2 times a week already. She informed that she left on a travel which she could not permit herself previously due to the disease—she left for her daughter for 3 months to Sakhalin. At the reception in 10 months the patient informed about rare aggravations once in 3-4 weeks, which are easily stopped by broncholythics. Taking into account that the state was stabilized and we managed to get remission, the needles were removed from auricular and corporal points.

EXAMPLE 8

Reflexogenic Zone within its Boundary

A 24 years old patient applied with a complaint for extra weight. During examination—expressed fat deposit according to gluteo-femoral type. Objectively—height 1.56, weight 90. A session of prolonged action upon AT 17-19 was conducted; hypo-calorie diet was prescribed. Next reception was appointed in a month. At the next reception—weight—minus 3 kg. Complaints for rich taste sensations even when taking tasteless not salted meals without species. The sensations stay in the form of gustatory feeling for a very long period of time. Gustatory memories and sometimes gustatory hallucinations are persecuting.

It was notice in practice that under action upon AT 17-18 (thirst, hunger) an appetite and sensation of thirst are blocked, but patients really frequently complain of rich, bright gustatory sensations and gustatory memory.

It is necessary to apply a prolonged action upon the zone of glossopharyngeal nerve which is located in the salivary gland zone. There are no acupuncture points in this zone, but it was noticed that during braking action to this zone gustatory sensations and salivation are reduced, because the sensitive fibers of this nerve perceive gustatory irritations and vegetative ones regulate salivation. Such variant of action as piercing zones of the basis of antilobium by the prolonged method with the acusal tract formation in the cartilage layer, gives an expressed therapeutical result in part of the patients, compared to classical piercing of AT 17-18. The patient had piercing upon this zone for action upon receptors 9 of the pair of the cranial nerve—glossopharyngeal nerve. The next reception was appointed in 1 month. On the third reception—the state is satisfactory. There were no complaints for previous symptoms. The weight decreased by 7 kg. Further on the patient was decreasing the weight stably feeling fine and lost weight up to the normal body mass (63 kg) in 6 months.

INDUSTRIAL APPLICABILITY

The application of the proposed method of acupuncture with a prolonged action permits to provide an effective treatment by non-medicamental method of a wide range of diseases, as well as raise the efficiency of acupuncture with a prolonged action at the expense of overcoming an effect of adaptation, changing the intensity of reflexogenic action, preventing complications, as well as expanding the selection of recipe used in treating different nosological forms. A possibility of using during method implementation of a simple and inexpensive equipment and a minimum of side affects permit to provide for a wide application of the proposed method in medical practice.

The invention claimed is:

1. A method of acupuncture with a prolonged action, during which acupuncture points are determined, pairs of points of needle entry and exit for at least one needle are selected, passing a needle made of material able to be plastically flattened through each of the selected entry and exit points of at least a pair of said pairs of points, leaving both ends of the at least one needle outside a patient's skin, fixing the at least one needle in this position by means of two locking members, installed on both ends of the at least one needle, and upon the end of acupuncture session leaving the at least one needle in the body of a patient for an assigned-time, wherein by means of a needle introduction an acusal tract is formed in at least one of a plurality of different histological layers of the patient's tissues, and entry and exit points for the at least one needle is selected at points located in the region including at least one of an acupuncture point, a reflexogenic zone and an indifferent zone;

wherein for fixing the needle, at least one of the locking members is provided with a through aperture and is configured to slide on the body of the needle, and the at least one locking member's fixation in an assigned position is carried out by a flattening plastic deformation of the body of the needle at a distal side of the at least one locking member so as the width of the flattened area exceeds the diameter of the said through aperture.

2. The method of claim 1 wherein the at least on of the plurality of the different histological layers is selected from the group comprising: epidermal layer, epidermis membrane, papillary layer, reticular layer, epichondral layer, cartilaginous layer, subcutaneous fat layer, muscle layer, ligaments, fascia or tendons.

3. The method of claim 1 wherein acupuncture is conducted for a plurality of sessions, and during conducting an acupuncture session, a plurality of needles are installed for a plurality of respective acusal tracts formation only in one of the different histological layers of the patient's tissues, and formation of acusal tracts in other of the different histological layers of the tissues is carried out by the introduction of a plurality needles during subsequent acupuncture sessions.

4. The method of claim 1 wherein during conducting an acupuncture session, needles are installed for acusal tracts formation in different histological layers of patient's tissues.

5. The method of claim 1 wherein acupuncture is conducted for a plurality of sessions, and during conducting at least one subsequent session of the plurality of acupuncture sessions, needles are installed for acusal tracts formation in one or several of the different histological layers after removal of needles installed during a previous session of the plurality acupuncture sessions, wherein at least one acusal tract is formed in different histological layers of the patient's tissues over the plurality of sessions.

6. The method of claim 1 wherein during conducting at least one subsequent session of a plurality of acupuncture sessions, needles are installed for acusal tracts formation in one or several histological layers without removal of needles installed during a previous session.

7. The method of claim 1 wherein the body of the needle is made of ductile metallic alloy.

8. The method of claim 3 wherein during conducting at least one subsequent session of the plurality of acupuncture sessions, needles are installed for acusal tracts formation in one or several histological layers after removal of needles installed during a previous session.

9. The method of claim 4 wherein during conducting at least one subsequent session of a plurality of acupuncture sessions, needles are installed for acusal tracts formation in one or several histological layers after removal of needles installed during a previous session.

10. The method of claim 3 wherein during conducting at least one subsequent session of the plurality of acupuncture sessions, needles are installed for acusal tracts formation in one or several histological layers without removal of needles installed during a previous session.

11. The method of claim 4 wherein during conducting at least one subsequent session of a plurality of acupuncture sessions, needles are installed for acusal tracts formation in one or several histological layers without removal of needles installed during a previous session.

* * * * *